US010695403B2

(12) United States Patent
Fouilloux-Meugnier et al.

(10) Patent No.: US 10,695,403 B2
(45) Date of Patent: Jun. 30, 2020

(54) USE OF FGF19 TO INCREASE MUSCLE FIBER SIZE

(71) Applicants: Universite Claude Bernard Lyon 1, Villeurbanne (FR); Institut National De La Recherche Agronomique (INRA), Paris (FR); Institut National De La Santé Et De La Recherche Médicale (INSERM), Paris (FR); Bergen Teknologioverforing AS, Bergen (NO)

(72) Inventors: Emmanuelle Fouilloux-Meugnier, Oullins (FR); Hubert Vidal, Saint Genis Laval (FR); Jérome Ruzzin, Morvik (NO)

(73) Assignees: Universite Claude Bernard Lyon, Villeurbanne (FR); Institut National de la Recherche Agronomique (INRA), Paris (FR); Institut National de la Santè et de la Recherche Médicale (INSERM), Paris (FR); Bergen Teknologioverforing AS, Bergen (NO)

( * ) Notice: Subject to any disclaimer, the term of this patent is extended or adjusted under 35 U.S.C. 154(b) by 55 days.

(21) Appl. No.: 15/739,238

(22) PCT Filed: Jun. 24, 2016

(86) PCT No.: PCT/EP2016/064671
§ 371 (c)(1),
(2) Date: Dec. 22, 2017

(87) PCT Pub. No.: WO2016/207354
PCT Pub. Date: Dec. 29, 2016

(65) Prior Publication Data
US 2018/0369331 A1 Dec. 27, 2018

(30) Foreign Application Priority Data
Jun. 25, 2015 (EP) .................... 15305990

(51) Int. Cl.
A61K 38/18 (2006.01)
A61K 45/06 (2006.01)
(52) U.S. Cl.
CPC .......... A61K 38/1825 (2013.01); A61K 45/06 (2013.01); A61K 2300/00 (2013.01)
(58) Field of Classification Search
None
See application file for complete search history.

(56) References Cited

U.S. PATENT DOCUMENTS 8,535,912 B2* 9/2013 Sonoda .............. A61K 38/1825
435/69.7
2007/0042395 A1* 2/2007 Botstein ................ C07K 14/50
435/6.16

FOREIGN PATENT DOCUMENTS

| WO | WO 99/27100 | 6/1999 |
|---|---|---|
| WO | WO 2007/100695 | 9/2007 |
| WO | WO 2011/047267 | 4/2011 |
| WO | WO 2013/006486 | 1/2013 |

OTHER PUBLICATIONS

Glass, David J., Cell Metabolism 26, 287-288, 2017.*
Benoit et al. Nature Medicine 23(8): 990-998, 2017.*
Aoyagi et al., *Cancer cachexia, mechanism and treatment*, 7(4) World J Gastrointest Oncol. 17-29 (Apr. 15, 2015).
Beenken et al., *The FGF family: biology, pathophysiology and therapy*, 8 Nature Reviews | Drug Discovery 235-253 (Mar. 2009).
Dostálová et al., *Plasma Concentrations of Fibroblast Growth Factors 19 and 21 in Patients with Anorexia Nervosa*, 93(9) J Clin. Endocrinol Metab 3627-3632 (Sep. 2008).
Ito et al., *Molecular cloning and expression analyses of mouse βklotho, which encodes a novel Klotho family protein*, 98 Mechanisms of Development 115-119 (2000).
Kir et al., *FGF19 as a Postprandial, Insulin-Independent Activator of Hepatic Protein and Glycogen Synthesis*, 331 Science 1621-1624 (Mar. 25, 2011).
Qin et al., *Dexamethasone-induced skeletal muscle atrophy was associated with upregulation of myostatin promoter activity*, 94 Research in Veterinary Science 84-89 (2013).
Walters et al., *A variant of FGF19 for treatment of disorders of cholestasis and bile acid metabolism*, 3(S1) Ann Transl Med 1-3 (2015).
Yousef et al., *Mechanisms of action of hESC-secreted proteins that enhance human and mouse myogenesis*, 6(8) Aging 602-620 (Aug. 2014).
*Muscle atrophy*, Wikipedia (Jun. 8, 2017).
Communication pursuant to Article 94(3) EPC dated Mar. 20, 2019, in corresponding European Patent Application No. 16 733 413.5-1112.
Official Action dated Dec. 7, 2015, in corresponding European Patent Application No. 15 305 990.2.
Communication pursuant to Article 94(3) EPC dated Jun. 26, 2018, in corresponding European Patent Application No. 15 305 990.2-1112.
International Search Report dated Sep. 6, 2016, in corresponding PCT Application No. PCT/EP2016/064671.
Witten Opinion dated Jun. 25, 2015, in corresponding PCT Application No. PCT/EP2016/064671.

* cited by examiner

Primary Examiner — Christine J Saoud
(74) Attorney, Agent, or Firm — Buchanan Ingersoll & Rooney PC

(57) ABSTRACT

The present invention relates to an FGF19 polypeptide for use in increasing muscle fiber size in the treatment of muscle atrophy in a mammal.

13 Claims, 7 Drawing Sheets
Specification includes a Sequence Listing.

USE OF FGF19 TO INCREASE MUSCLE FIBER SIZE

CROSS-REFERENCE TO RELATED APPLICATIONS

This application is a U.S. National Stage Application pursuant to 35 U.S.C. § 371 of International Patent Application PCT/EP2016/064671, filed on Jun. 24, 2016, and published as WO 2016/207354 on Dec. 29, 2016, which claims priority to European Patent Application 15305990.2, filed on Jun. 25, 2015, all of which are incorporated herein by reference in their entireties for all purposes.

The present invention relates to the field of muscle mass loss, associated with diseases or medical conditions. The present invention relates also to the field of compounds used for increasing the muscle mass in animal or human bodies.

PRIOR ART

There are a number of conditions in which muscle wasting occurs. It may result from specific diseases, from conditions such as long-term immobilization, or from normal ageing of the body.

Many diseases are characterized by a loss of lean mass and/or of muscle mass, such as neuromuscular diseases, in particular muscular dystrophies. The loss of strength is usually accompanied by muscular wasting, also known as amyotrophia or muscle atrophy.

The loss of muscle mass and/or of lean mass may also be associated with a causal disease or event, such as muscle dystrophy following a stroke, or a cachexia syndrome, also called marasmus.

Cachexia is a complex metabolic syndrome associated with an underlying disease, characterized by a loss of body mass, especially of muscle, that cannot be reversed nutritionally. Clinically, cachexia is more precisely defined by an involuntary loss of weight, muscle atrophy, fatigue, weakness, and a significant loss of appetite. In children it is represented by failure to thrive.

Cachexia is seen in many medical conditions, including cancer, acquired immunodeficiency syndrome (AIDS), chronic obstructive pulmonary disease, multiple sclerosis, chronic heart failure, tuberculosis, familial amyloid polyneuropathy, mercury poisoning and hormonal deficiency.

It is estimated that half of all patients with cancer eventually develop a syndrome of cachexia, with a progressive loss of adipose tissue and of the skeletal muscle mass. Cancer cachexia is characterized by systemic inflammation, a negative energy balance, and anorexia. This syndrome is associated with poor responses to chemotherapy and a decreased survival.

Cachexia is still an underestimated and untreated condition. Proposed therapies for cachexia include appetite stimulants, palliation of symptoms and reduction of the distress of patients. Combination therapy with diet modification and/or exercise has been added to novel pharmaceutical agents, such as Megestrol acetate, medroxyprogesterone, ghrelin, omega-3-fatty acid among others. An extensive list of possible therapies is presented in the review from (Aoyagi et al., 2015). However, other therapeutic compounds are actively researched to treat this syndrome.

Other medical conditions induce a significant loss of muscle mass, such as anorexia, hyperthyroidism, and alcoholism. Loss of muscle mass can also be a side effect of drugs such as corticosteroids.

Although not always considered as "pathological", some other situations are associated with muscle wasting.

The ageing of bodies leads to a loss of muscle mass and/or lean mass. Indeed, as the body ages, an increasing proportion of skeletal muscle is replaced by fibrous tissue. Therefore, normal ageing in mammals is associated with a progressive decrease in skeletal muscle mass and strength, a condition referred to as sarcopenia. It has been shown that sarcopenia is caused by a loss of muscle fibers, but also by a reduction in fiber size, particularly among type II fibers. This phenomenon is also called "fiber atrophy". Sarcopenia is responsible for decreased levels of physical activity which, in turn, can result in increased body fat and a further loss of muscle.

Sarcopenic individuals, in their relatively weaker state, may be more prone to fall, and have decreased bone and joint health, which further limits mobility. Consequently, in this condition, a further loss of muscle mass, and in particular of fiber atrophy, is to be prevented, especially in the elderly.

Long term immobilization, due to illness or disability, are also causing muscle loss. These immobilizations may have various causes such as confinement in a wheelchair, prolonged bed rest, bone fracture or trauma. It is estimated that bed-rest after surgery causes loss of skeletal muscle mass in a body of approximately 10% per week.

Drugs such as glucocorticoids have an effect on muscle mass: muscle atrophy is induced after a few days of treatment. As in sarcopenia, this atrophy is caused both by a loss of muscle fibers, and a reduction in fiber size.

Untreated muscle wasting disorders can have serious health consequences. The changes that occur during muscle wasting lead to a weakened physical state, seriously limiting the rehabilitation of patients from immobilizations. Despite the clinical importance of the condition, few treatments exist to prevent or reverse the condition.

Preventing muscle atrophy and/or increasing muscle mass can also be desirable for non-therapeutic issues.

In the area of food production, increasing the muscle of livestock animals is highly desirable to increase the profitability level of the meat production.

In the area of human well-being, development of muscle mass and body fitness is a multi-billion dollar industry worldwide. Nutraceutical supplements and drugs are utilized by populations seeking to restore, augment or repair body tissues for both aesthetic and athletic purposes. Fitness devotees and athletes seek to increase stamina, strength and muscle force in order to enhance personal appearance and/or performance. Aiming to aesthetically add muscle to body mass, replace fat with muscle or to simply increase strength in order to reduce fatigue stamina and/or appearance, is accepted as a legitimate concern for good physiological and psychological health.

For professional space travelers, called astronauts or cosmonauts, the prevention of muscle atrophy is also of primary importance. Indeed, lack of gravity in space induces a significant muscle atrophy in human bodies; a compound preventing such loss of muscle, and therefore loss of muscular strength, would be highly appreciated among people submitted to space conditions. For at least these reasons, compounds increasing muscle fibers size, and therefore inducing an increase of muscle mass and/or reducing the loss of muscle mass in a mammal body are actively searched and studied.

Inventors have now identified the role of a specific growth factor, called Fibroblast Growth Factor 19 (FGF19) in humans and Fibroblast Growth Factor 15 (FGF15) in mice, in the development and maintenance of muscle mass in mammal bodies, in particular its action on the muscle fibers whose surface and size increase under the action of this growth factor.

FGF19 was known to play an important role in hepatic bile homeostasis and cholesterol homeostasis. FGF19 lowers serum glucose and triglycerides, increases metabolic rate and reverses dietary and leptin-deficient diabetes in mice (Fu et al., 2004). FGF19 also stimulates hepatic protein and glycogen synthesis (S Kir et al., 2011). In addition, FGF19 lowers gluconeogenesis and fatty acid oxidation (Potthoff et al., 2011).

FGF19 has been previously reported as beneficial for treating muscle injuries (Yousef et al., 2014). It has been shown that FGF19 stimulates the multiplication of myoblasts, undifferentiated progenitor cells of the muscle, in injured muscles. However, FGF19 effects on differentiated muscle cells, called myotubes, and forming muscle fibers, were unknown up to now.

Although the role of FGF19 was up to now limited to metabolic functions or to muscle injury cases, novel therapeutic and non-therapeutic uses of FGF19 are hereby presented, related to its ability to act as an agent increasing muscle fiber size.

SUMMARY OF THE INVENTION

The invention concerns a FGF19 polypeptide for its use as an agent increasing muscle fibers size in the prevention and/or treatment of loss of muscle mass, also designated as muscle atrophy, in a mammal body.

The invention also concerns a FGF19 polypeptide for its use as a drug for increasing muscle fibers size in a mammal body, wherein it induces an increase of muscle mass in the mammal body.

The invention also concerns a pharmaceutical composition comprising at least a FGF19 polypeptide and a pharmaceutical vehicle, for its use in the prevention and/or treatment of loss of muscle mass, and especially muscle atrophy in a mammal body.

More precisely, the invention concerns:
- the use of FGF19 polypeptide as an agent increasing muscle fibers size in the prevention and/or treatment of muscle wasting associated with diseases or syndrome such as cachexia, or sarcopenia in the population of elderly;
- the use of FGF19 polypeptide as an agent increasing muscle fibers size to increase muscle mass in an animal body, in particular cattle, in order to increase meat production;
- the use of FGF19 polypeptide as an agent increasing muscle fibers size to increase muscle mass in a human body, for aesthetical or athletical purposes, or for space travelers; and
- a pharmaceutical composition comprising at least a FGF19 polypeptide and a pharmaceutical vehicle, for its uses as listed above.

(B) mRNA expression of FGFR4 and β-KLOTHO in mice soleus and gastrocnemius muscles (Nr1i2$^{+/+}$ in grey columns and Nr1i2$^{-/-}$ in black columns).

(C) mRNA expression of FGFR4 and β-KLOTHO in human myoblasts (undifferentiated muscle cells) and in human myotubes prepared from control healthy subjects.

Figure 2:
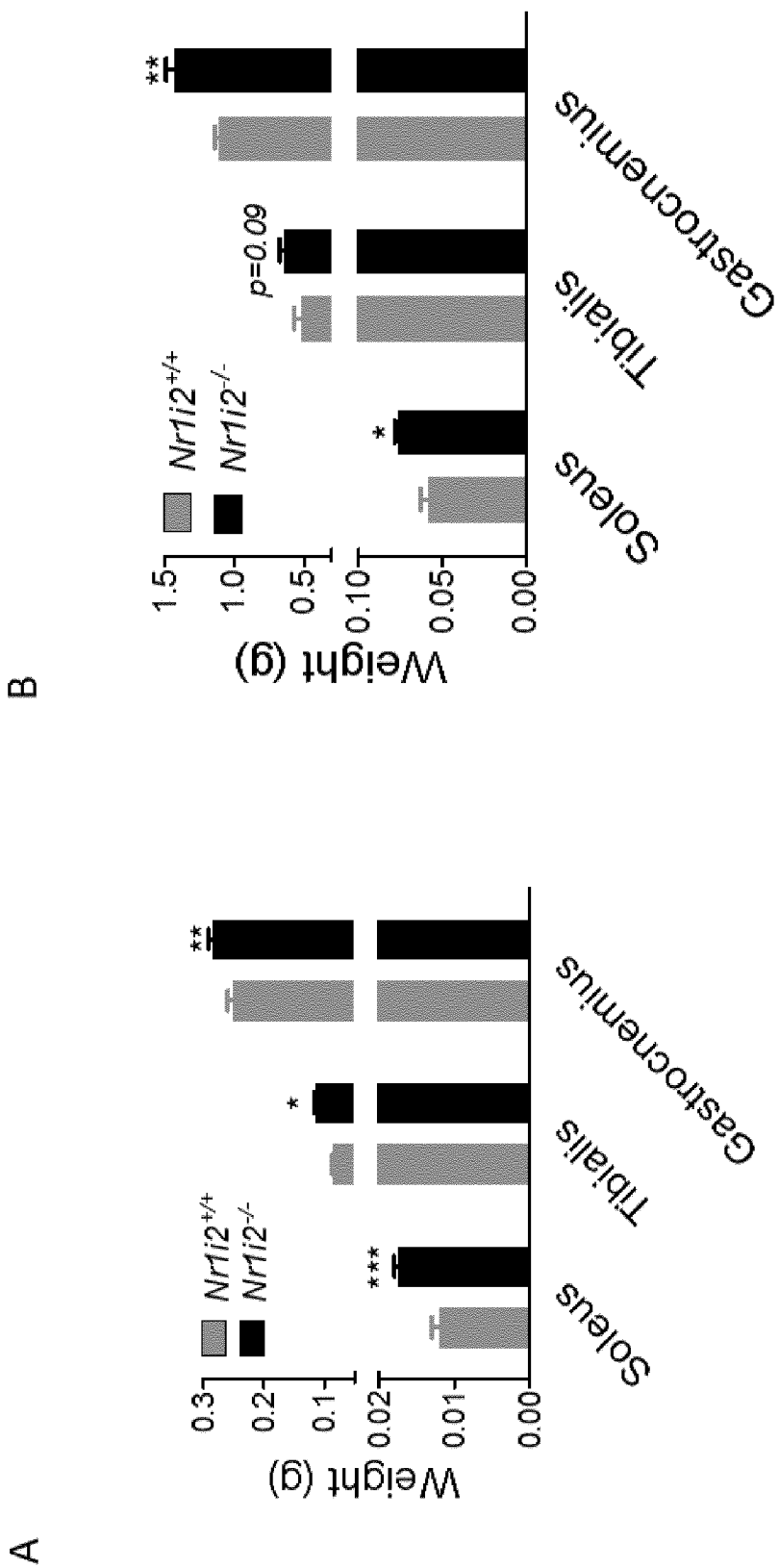

FIG. 2. Weights of skeletal muscles in mice with high level of FGF15

(A) Weights of skeletal muscles (soleus, tibialis and gastrocnemius) of Nr1i2$^{+/+}$ (grey) and Nr1i2$^{-/-}$ (black) mice of 22 weeks of age and that are fed a control diet (n=6).

(B) Weights of skeletal muscles: soleus, tibialis and gastrocnemius, of Nr1i2$^{+/+}$ (grey) and Nr1i2$^{-/-}$ (black) mice of 17 months of age, that are fed a control diet (n=5).

Figure 3:
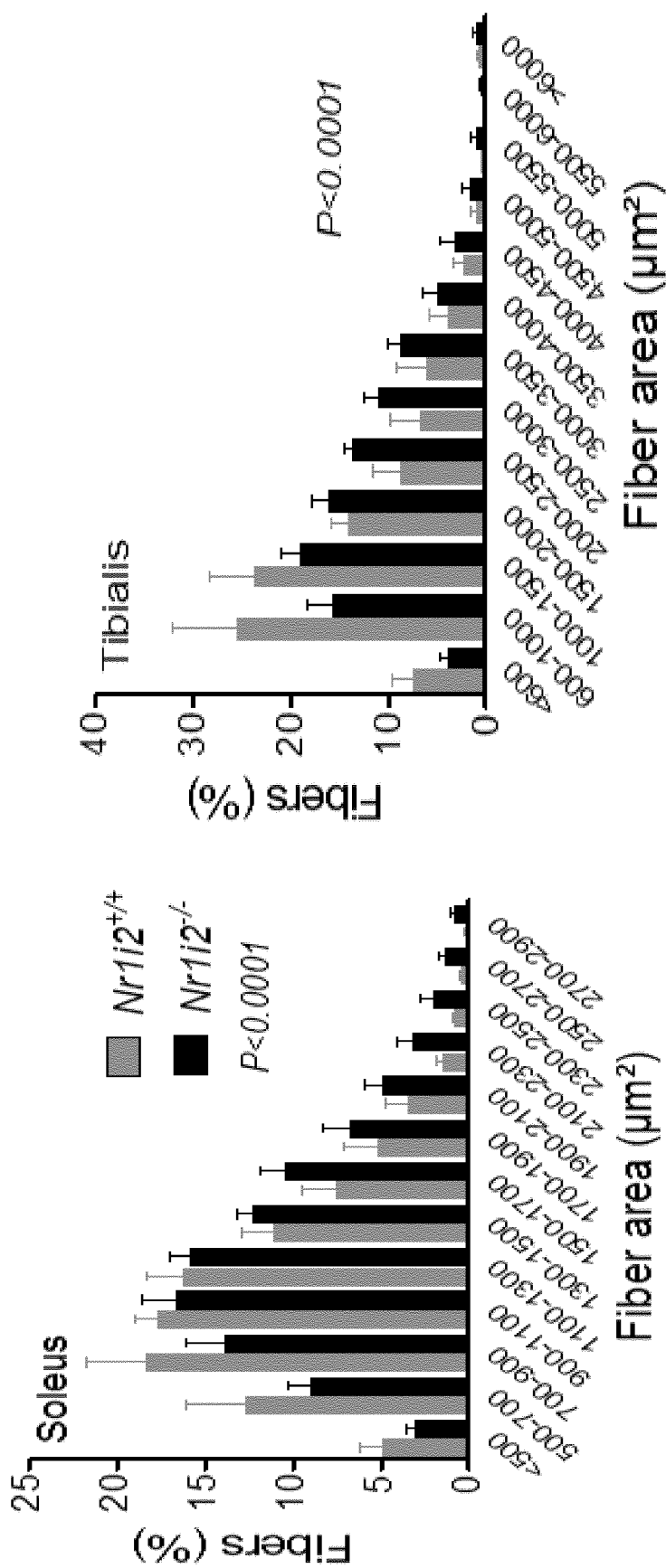

FIG. 3. Sizes of muscular fibers in mice with high level of FGF15

Nr1i2$^{+/+}$ (grey columns) and Nr1i2$^{-/-}$ (black columns) mice were fed a control diet for 22 weeks.

(A) Frequency distribution of areas from laminin stained muscle fibers in soleus.

(B) Frequency distribution of areas from laminin stained muscle fibers in tibialis.

Figure 4:
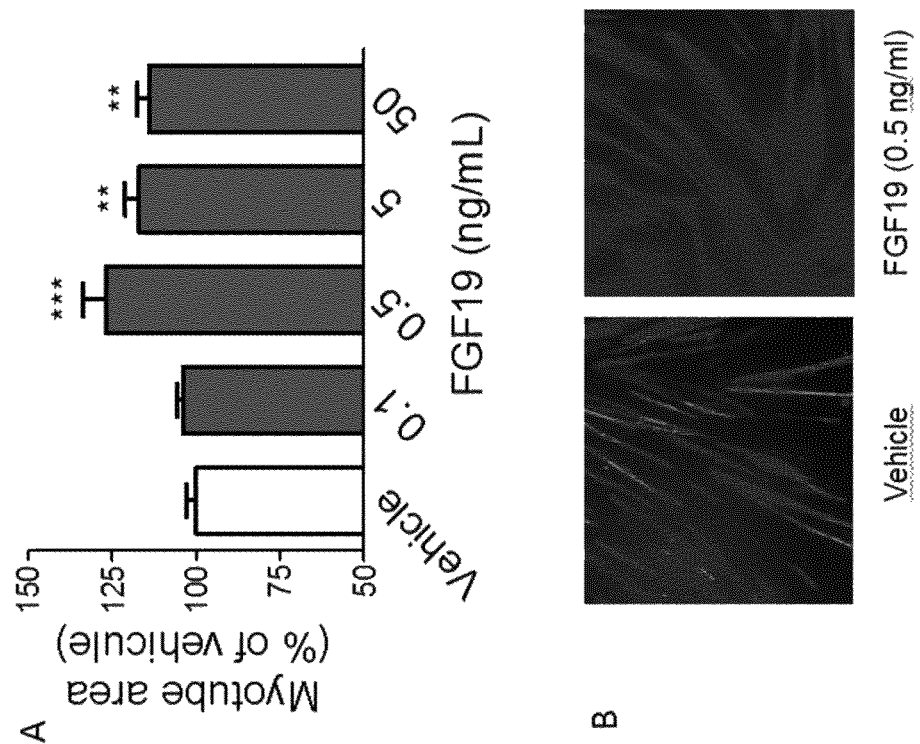

FIG. 4. Effects of recombinant FGF19 on human myoblasts cultured in vitro

Human myotubes were daily treated for 6 days with the vehicle only (white bars) or with FGF19 diluted in the vehicle (at 0.1, 0.5, 5 or 50 ng/mL; grey bars).

(A) The histogram represents the myotube area (per field of view and as a percentage of the value measured in the vehicle condition (n=6)

(B) The pictures are representative images of myosine staining of myotubes allowing estimation of the myotube area.

Figure 5:
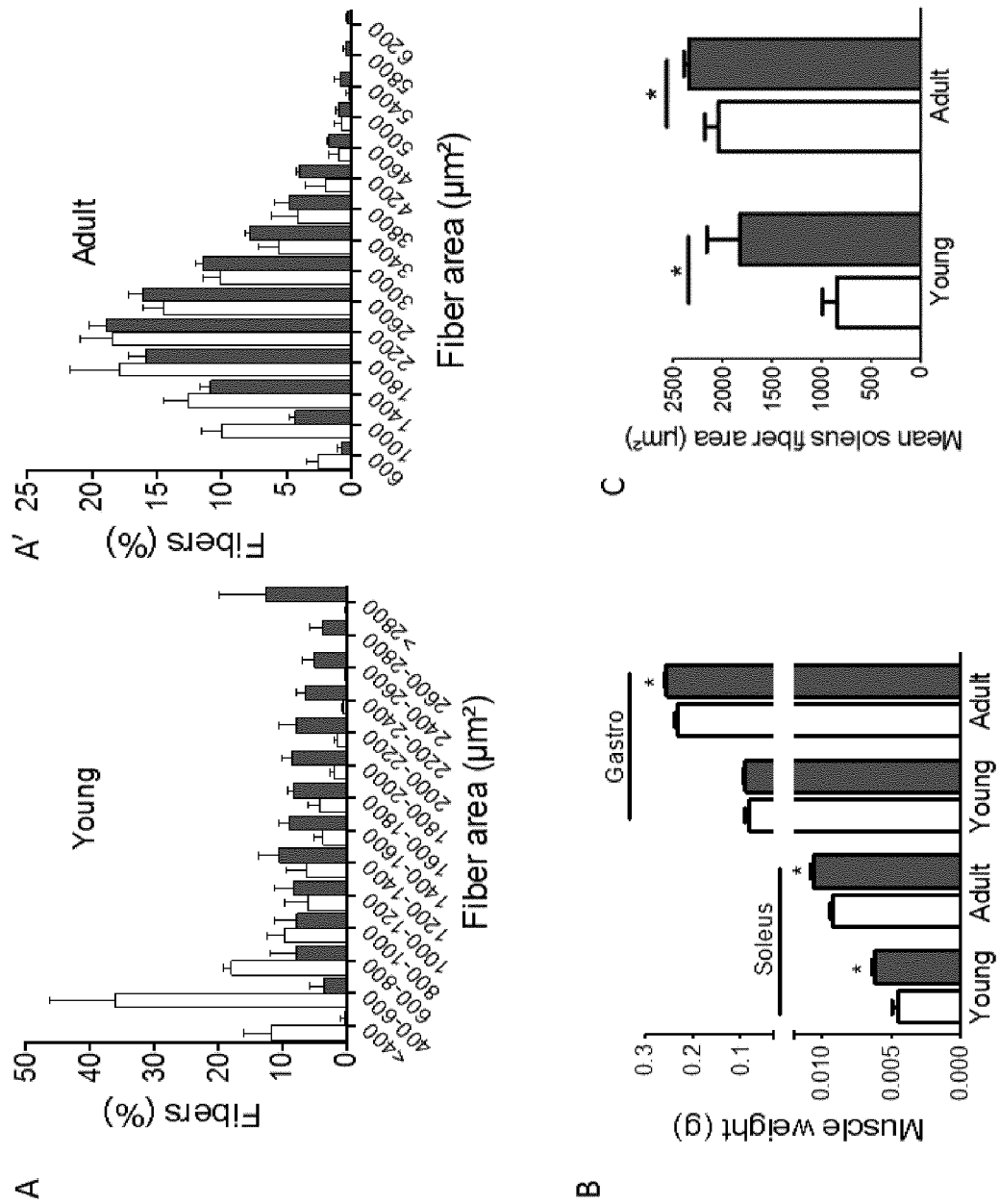

FIG. 5. Effects of injections of recombinant FGF19 on muscle of mice in vivo

Young (3 week-old) and adult (18 week-old) normal wild type mice were daily treated with vehicle or human recombinant FGF19 (for 7 days, 0.1 mg/kg, subcutaneous injections, n=4-5).

(A) Fiber size distribution in soleus, in young mice treated with vehicle (white column) or FGF19 (grey columns).

(A') Fiber size distribution in soleus, in adult mice treated with vehicle (white column) or FGF19 (grey columns).

(B) Weight changes of soleus and gastrocnemius muscle, in young and adult mice treated with vehicle (white columns) or FGF19 (grey columns).

(C) Mean of muscle fibers area, in soleus muscle, in young and adult mice treated with vehicle (white columns) or FGF19 (grey columns).

Figure 6:
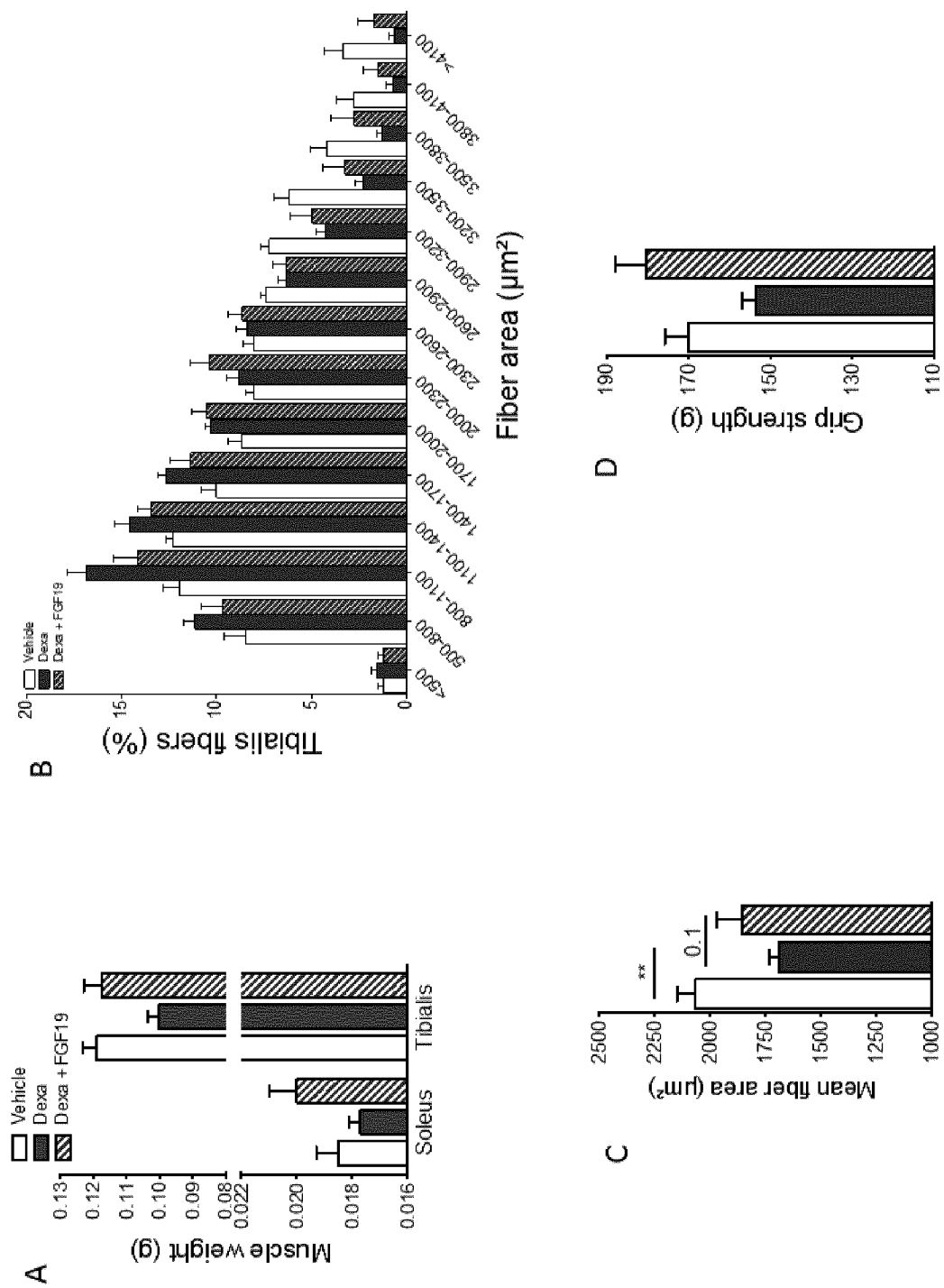

FIG. 6. Effects of injections of FGF19 on muscle in dexamethasone induced muscle atrophy in mice C57BL/6 mice (23-week-old) were treated with dexamethasone (25 mg/kg) and dexamethasone plus FGF19 (0.1 mg/kg) for 14 days. As negative controls, mice were treated with a pharmaceutically acceptable excipient designated as "vehicle".

White bars represent the results obtained in vehicle-treated mice, grey bars represent the results obtained in dexamethasone-treated mice, and stripped bars represent the results obtained with dexamethasone and FGF19-treated mice. Distributions are analyzed using Kolmogorov-Smirnov test with P<0.01.

(A) Muscle weight (in grams)
(B) Fiber size distribution in tibialis
(C) Mean of muscle fibers area in tibialis muscle
(D) Grip strength of treated-mice.

Figure 7:
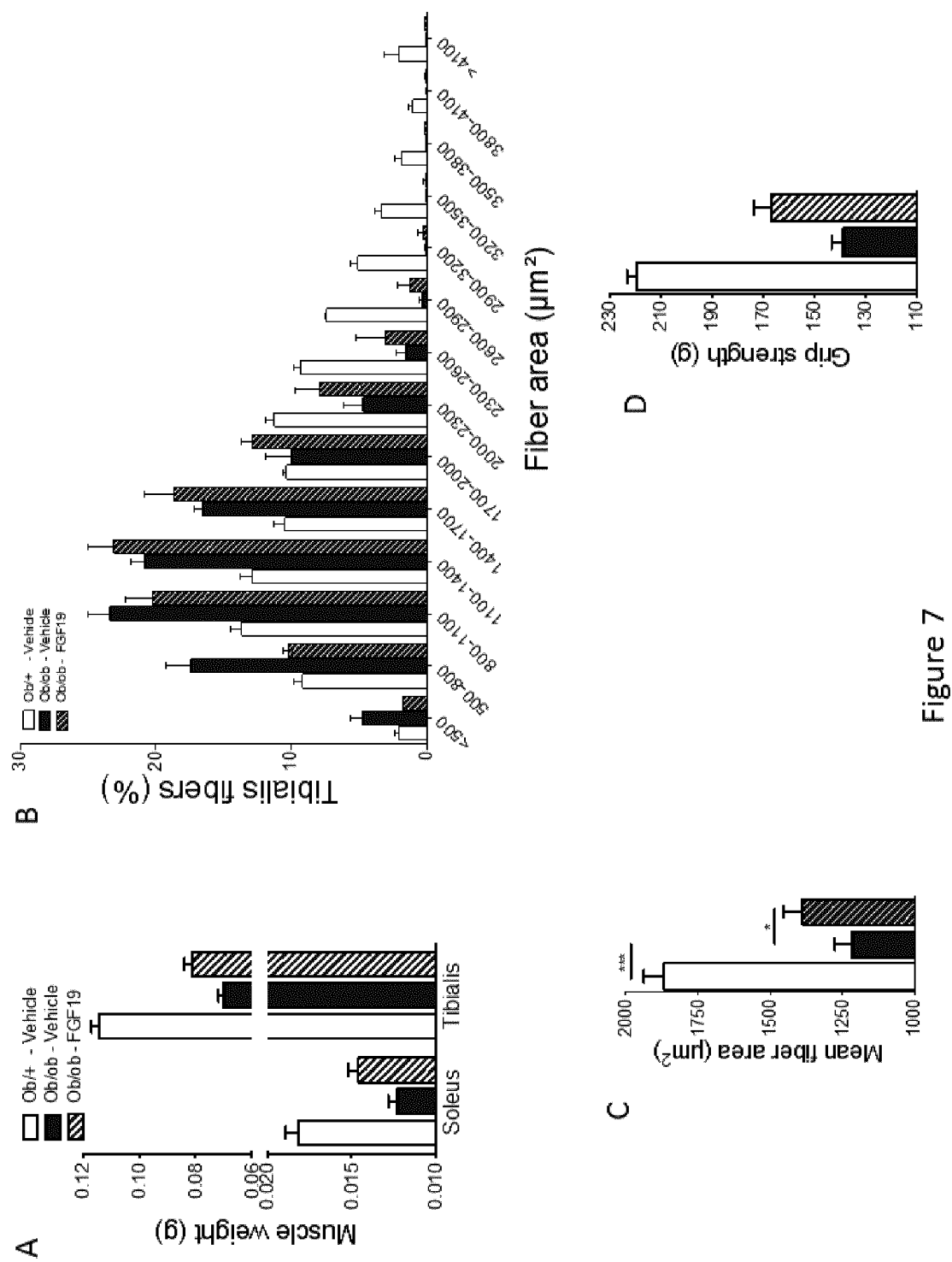

FIG. 7. Effects of injections of FGF19 on muscle in a model of obesity induced muscle atrophy in mice ob/ob mice (13-week-old), an animal model for obesity, were daily treated with FGF19 (0.1 mg/kg) for 7 days. Negative controls are ob/+ mice (non obese) and ob/ob mice treated with the vehicle.

White bars represent the results obtained in ob/+ mice, grey bars represent the results obtained in vehicle-treated mice, and stripped bars represent the results obtained with FGF19-treated ob/ob mice. Distributions are analyzed using Kolmogorov-Smirnov test with P<0.01.

(A) Muscle weight (in grams) of soleus and tibialis muscles
(B) Fiber size distribution in tibialis
(C) Mean of muscle fibers area in tibialis muscle
(D) Grip strength of treated-mice.

DETAILED SPECIFICATION OF THE INVENTION

All technical terms used in the present specification are well known by the man skilled in the art, and are extensively defined in the reference manual from Sambrook et al. entitled «Molecular Cloning: a Laboratory Manual».

The present application relates to a FGF19 polypeptide for its use as an agent increasing muscle fibers size, in the prevention and/or treatment of loss of muscle, also designated muscle atrophy, and/or loss of lean mass in a mammal body.

FGF19 Polypeptide

In the sense of the invention, the term "FGF19 polypeptide" means a polypeptide, i.e. a chain of amino acids, such as described below.

FGF19, also called FGF15 in rodents, is a member of a subfamily of fibroblast growth factors that govern nutrient metabolism. FGF19 is expressed and secreted in the distal small intestine, by the biliary and intestinal epithelium cells, where its synthesis is up-regulated after the postprandial uptake of bile acids. Therefore, in response to feeding, the concentration of circulating FGF19 increases in the body.

FGF19 exerts its action on the liver and in other tissues toward the activation of FGF receptors and the co-receptor Klotho beta (Lin et al., 2007).

According to the invention, the terms "FGF19 polypeptide", "FGF19" and "FGF15/19" designate the native sequence of a naturally-occurring form of a polypeptide FGF19 such as expressed in any mammal organism. This term includes any naturally-occurring isoform, which encompass the variant forms such as alternatively spliced forms, the allelic variant forms, and both unprocessed and processed forms of FGF19, such as the forms of FGF19 polypeptide comprising a signal peptide.

This term "FGF19 polypeptide" also includes fragments of a naturally-occurring form of a polypeptide FGF19, in particular recombinant fragments having the same biological activity than said naturally-occurring form.

This term does not include chimeric FGF19 polypeptides, such as chimeric polypeptides comprising portions of the FGF19 polypeptide fused with other sequence portions from another FGF polypeptide.

A FGF19 polypeptide according to the invention can be isolated from sources where it is naturally-occurring, such as fluids and tissues of an organism. In this case, the FGF19 polypeptide is isolated, i.e. separated from its natural environment.

In another embodiment, a FGF19 polypeptide according to the invention can be produced by recombinant and/or synthetic means, as well known by the man skilled in the art. Advantageously, the FGF19 polypeptide produced by recombinant microorganisms is purified from the culture medium.

Human recombinant FGF19 polypeptide is available commercially, for example from R&D Systems (UK).

In the sense of the invention, the FGF19 polypeptide presents the ability to bind to at least one of its FGF receptors and the co-receptor Klotho beta (Lin et al., 2007).

In the sense of the invention, the term "FGF19 polypeptide" includes all FGF19 polypeptides presenting at least 50% of identity with the human sequence shown in SEQ ID NO. 1.

The phrase "a FGF19 polypeptide presenting at least 50% of identity with the human sequence shown in SEQ ID NO. 1" designates a polypeptide, member of the FGF19 family, having an amino acid sequence presenting at least 50% of amino acid identity with the reference sequence. This requires that, following alignment, 50% of the amino acids in the candidate sequence are identical to the corresponding amino acids in the reference sequence.

By 'identity of amino acid' is meant that the same amino acid is observed on both sequences. Identity does not take account of post-translation modifications that may occur on amino acids. Identity according to the present invention is determined by aid of computer analysis, such as the ClustalW computer alignment program, and the default parameters suggested therein. The ClustalW software is available from the website http://www.clustal.org/clustal2/. By using this program with its default settings, the part of a query and of a "reference polypeptide" are aligned. The number of fully conserved residues are counted and divided by the length of the reference polypeptide. According to the present invention, the "reference polypeptide" presents the sequence as shown in SEQ ID NO. 1.

The terms "at least 50% of identity" indicates that the percentage of identity between both sequences, the query and the reference polypeptide of SEQ ID NO. 1, is of at least 50, 55, 60, 65, 70, 75, 80, 85, 86, 87, 88, 89, 90, 91, 92, 93, 94, 95, 96, 97, 98, 99 or 100%.

Accordingly, the FGF19 polypeptide is chosen among the FGF15 polypeptide expressed in mice, the FGF19 polypeptide expressed in human, or the homologues of FGF15 and FGF19 expressed in other mammals such as rat, dog, cat, sheep, cattle, horse, pig, goat, rabbit, etc.

Members of the FGF19 family include in particular:
the human FGF19 polypeptide of 216 amino acids (including 24 amino acids constituting the signal peptide) whose sequence is shown in SEQ ID NO. 1;
the *mus musculus* FGF15 polypeptide of 218 amino acids (including 25 amino acids constituting the signal peptide) whose sequence is shown in SEQ ID NO. 10.

According to a particular embodiment of the invention, the FGF19 polypeptide presents a sequence chosen among anyone of the sequences as shown in SEQ ID NO.1, 2, 3, 4, 5, 6, 7, 8, 9, or 10, as presented in the table 1 below.

According to another embodiment, the FGF19 polypeptide is a fragment of a polypeptide presenting a sequence chosen among anyone of the sequences as shown in SEQ ID NO.1, 2, 3, 4, 5, 6, 7, 8, 9, or 10, as presented in the table 1 below.

TABLE 1

| Sequence Number | Species | Length in amino acids | Identity with SEQ ID NO. 1 |
|---|---|---|---|
| SEQ ID NO. 1 | Homo sapiens | 216 | 100% |
| SEQ ID NO. 2 | Sus scrofa | 220 | 75.93% |
| SEQ ID NO. 3 | Bos taurus | 218 | 73.95% |
| SEQ ID NO. 4 | Equus caballus | 94 | 90.43% |
| SEQ ID NO. 5 | Ovis aries | 137 | 73.72% |
| SEQ ID NO. 6 | Canis familiairis | 193 | 80.31% |
| SEQ ID NO. 7 | Felis cattus | 219 | 81.94% |
| SEQ ID NO. 8 | Oryctolagus cuniculus | 219 | 72.56% |
| SEQ ID NO. 9 | Rattus norvegicus | 218 | 53.11% |
| SEQ ID NO. 10 | Mus musculus | 218 | 52.63% |

In the sense of the invention, the phrase "as an agent increasing muscle fibers size" designates the in vivo technical effect of FGF19 on muscle differentiated cells, also referenced as myotubes or muscle fibers. This technical effect is demonstrated in the examples of the present application.

The "increasing size effect" means that, compared to muscle fibers of untreated mice, the mean fiber area is superior of at least 10% of the mean fiber area of untreated mice. For example, in FIG. 5C, in adult mice, the mean fiber area of untreated mice is less than 2100 $\mu m^2$; although the mean fiber area of FGF19-treated mice is about 2350 $\mu m^2$, corresponding to an increase of the fiber area of about 11.9% ($^{250}/_{2100}$).

In the present application, the terms "fiber size" and "fiber area" are used interchangeably and designate both the surface of the muscle fiber.

Measuring the size of the muscle fiber may be performed according to techniques well known by the man skilled in the art.

A preferred method comprises a step of measuring in vitro the muscle fiber size of a large set of muscle fibers from a muscle tissue sample of a tested mammal, whereby a set of muscle fiber size values are provided. In preferred embodiments, the said muscle tissue sample consists of one or more transversal cross-sections of muscle tissue.

According to preferred embodiments of the measuring method, the muscle fibers of the said tissue sample are pre-treated so as to perform the size measuring more easily. According to these preferred embodiments, the muscle fibers are pre-treated by muscle fibers staining, according to known methods. Muscle fibers staining methods encompass immuno-staining methods wherein one or more antibodies directed to a muscle protein are brought into contact with the muscle tissue sample so as to increase detectability of the muscle fibers and thus facilitate measuring the muscle fiber size. In some embodiments the said one or more antibodies are labeled antibodies. In some other embodiments, the said one or more antibodies are non-labeled antibodies. In preferred embodiments, the staining step comprises bringing the muscle tissue sample into contact with antibodies directed to a muscle protein selected in a group comprising laminin and myosin. Illustratively, the one skilled may use the anti-laminin antibody #L9393 commercialized by the Company Sigma-Aldrich (Saint Quentin Fallavier, France).

In preferred embodiments, the size of a muscle fiber is then measured under microscopy. In most preferred embodiments, a muscle fiber size is measured automatically by using a microscope apparatus allowing capture of digital images, and optionally by using also an image analysis computer program.

Then, a statistical test for assessing the existence of a difference between (i) muscle fiber size values determined for a first muscle tissue sample and (ii) muscle fiber size values determined for a second muscle tissue sample is performed.

Most preferably, the difference in muscle fiber size between two distinct muscle tissue samples (e.g. between (i) a muscle tissue sample collected from a non-treated individual and (ii) a muscle tissue sample collected from an individual treated with a FGF19 polypeptide) is assessed using Kolmogorov-Smirnov test which is well-known in the art.

Prevention and/or Treatment of Loss of Muscle Mass

According to the invention, the term "muscle mass" could be replaced either by "muscle weight" or "muscle volume".

A mammal body is constituted of different types of tissues, basically classified as: epithelial, connective, nervous and muscular tissue.

The present invention relates to a loss of weight/mass in mammal bodies, specifically related to a loss of muscular tissue mass. It also relates to a loss of lean mass, which designates the weight of the body calculated by subtracting body fat weight from total body weight.

Muscle or "muscular tissue" is a soft tissue found in all mammals. There are three types of muscle: skeletal, cardiac, and smooth. An average adult male is made up of 42% of skeletal muscle and an average adult female is made up of 36% (as a percentage of body mass).

Skeletal muscles are further divided into two broad subtypes: slow twitch (type I) and fast twitch (type II) fibers.

Type I or "red" muscle is dense, is rich in mitochondria and myoglobin, giving the muscle tissue its characteristic red color. It can carry more oxygen and sustain aerobic activity using fats or carbohydrates as fuel. Slow twitch fibers contract for long periods of time but with little force.

Type II muscle or "fast twitch" comprises fibers that contract quickly and powerfully, but fatigue very rapidly, sustaining only short, anaerobic bursts of activity before muscle contraction becomes painful. They contribute most to muscle strength and have greater potential for increase in mass.

The phrase "loss of muscle mass" and "muscle atrophy" are used interchangeably in the present application. Both phrases designate, according to the invention, a decrease in the mass of the muscular tissue of any type: skeletal, cardiac, and/or smooth muscle. The present invention relates mainly to the prevention and/or treatment of skeletal muscle atrophy.

This muscle atrophy induces a loss of total body weight, meaning a loss of the lean mass that is optionally accompanied with a loss of the body fat.

In a mammal body, the loss of muscle mass can be sudden or progressive. The loss of muscle mass can be voluntary or involuntary. In a specific aspect of the invention, the loss of muscle mass is involuntary.

The percentage of loss of muscle mass can be measured in percentages of loss compared to the muscle mass observed at a precedent moment (To). For example, the loss of muscle mass is a loss of at least 5%, 10%, 15%, 20%, 25%, 30%, 35%, 40% or even 45% of the total muscle mass of the body as measured in said precedent moment.

According to a specific embodiment, the invention relates to a FGF19 polypeptide for its use as an agent increasing muscle fibers size in the prevention of muscle atrophy, in a mammal body.

According to another specific embodiment, the invention relates to a FGF19 polypeptide for its use as an agent increasing muscle fibers size in the treatment of muscle atrophy, in a mammal body.

Equivalence Between Muscle Mass and Lean Mass Body

The term "lean body mass" (LBM) designates a component of body composition, that is calculated by subtracting body fat weight from total body weight.

Therefore, the "lean body mass" includes the weight of all body components (muscle, bones, blood, nervous tissues, etc) at the strict exclusion of the fat component.

Since the weight of bones, blood, nervous tissues, etc is not variable, when the lean body mass decreases, it is mainly related to a decrease in the muscle weight of the body.

Therefore, the measure of the "decrease" or "increase" of muscle mass in a body can be easily evaluated from the measure of the lean mass of the body, said LBM being evaluated at at least two time points $T_0$ and $T_1$.

The lean body mass is usually estimated using mathematical formulas. In particular, the following formula may be used:

For men: $LBM=(0.32810*W)+(0.33929*H)-29.5336$

For women: $LBM=(0.29569*W)+(0.41813*H)-43.2933$ where W is body weight in kilograms, and H is body height in centimeters.

According to an embodiment of the invention, the loss of muscle mass corresponds to a loss of lean body mass as measured as described above, the lean body mass being measured at a time point $T_0$ and then at a time point $T_1$, the period between $T_0$ and $T_1$ being a significant period of time of about two weeks, three weeks, a month, two months, three months, four months, five months, six months, seven months, eight months, nine months, ten months, eleven months, twelve months, fifteen months, eighteen months, two years, three years, four years, or five years.

In the sense of the invention, the term "prevention" designates an approach for preventing the loss of muscle and/or lean mass in the mammal body.

In the sense of the invention, the term "treatment" or "treating" designates an approach for obtaining beneficial clinical results on the muscle mass, in particular diminishing the extent of the loss, stabilizing the loss (e.g., preventing or delaying the worsening of the loss of muscle mass), delaying or slowing the loss of muscle mass, and/or increasing the muscle mass.

According to the invention, the term "mammal" refers to any animal classified as a mammal, including humans, domestic and farm animals, and zoo, sports, or pet animals, such as dogs, cats, cattle, horses, sheep, pigs, goats, rabbits, etc.

In a first embodiment of the invention, the mammal body is a human body.

In a second embodiment of the invention, the mammal body is a non-human mammal body.

Medical Conditions Inducing a Loss of Muscle Mass

According to one of its specific embodiment, the invention is related to the prevention and/or treatment of the loss of muscle mass, also designated as muscle atrophy, or of the loss of the lean mass, in a human body, this loss being due to specific medical conditions.

This medical condition is preferentially a medical condition diagnosed by a qualified practitioner. A medical condition can also be auto-diagnosed by the individual presenting the condition.

According to a first aspect of the invention, the medical condition causing the loss of muscle mass, also designated as muscle atrophy, in a human body is cachexia.

Cachexia is a complex metabolic syndrome associated with an underlying disease, characterized by a loss of body mass, especially of muscle, that cannot be reversed nutritionally.

In a particular embodiment of the invention, the medical condition causing the loss of muscle mass in a human body is cancer cachexia, a syndrome of cachexia wherein the underlying disease is cancer.

According to a second aspect of the invention, the medical condition causing the loss of muscle mass, also designated as muscle atrophy, in a human body is sarcopenia, a medical condition linked to the ageing of the body.

In humans, ageing refers to a multidimensional process of physical, psychological, and social change. Ageing corresponds to the natural process of becoming older. Ageing of the body represents the accumulation of changes in a body over time. The term "ageing of the body" relates to the physical changes of the body when the body gets old.

In particular, "ageing of the body" can be considered as the physical changes that appear when the human body reaches 70 years; 75 years; 80 years; 85 years; 90 years; 95 years; 100 years; 105 years or more.

According to a third aspect of the invention, the medical condition causing the loss of muscle mass, also designated muscle atrophy, in a human body is a prolonged immobilization of the body.

A "prolonged" or "long term" immobilization corresponds to an immobilization of the body for at least one week, two weeks, three weeks, four weeks, one month, two months, three months, four months, five months, six months, seven months, eight months, nine months, ten months, eleven months, twelve months, fifteen months, eighteen months, two years, three years, four years, five years or more than five years.

The immobilization may have various causes such as confinement in a wheelchair, prolonged bed rest, bone fracture or trauma.

According to a fourth aspect of the invention, the medical condition causing the loss of muscle mass, also designated muscle atrophy, in a human body is another medical condition such as obesity, anorexia, hyperthyroidism, alcoholism, or is related to side effects of drugs such as corticosteroids.

According to a specific embodiment, the present invention relates to a method for treating an individual presenting a loss of muscle mass, also designated muscle atrophy, and/or a loss a lean mass, comprising the administration to said individual of an efficient amount of a FGF19 polypeptide, as an agent increasing muscle fibers size.

According to another specific embodiment, the present invention relates to the use of a FGF19 polypeptide, as an agent increasing muscle fibers size, for the manufacture of a medicament for the prevention and/or treatment of loss of muscle mass, also designated muscle atrophy, in a mammal body.

Increase of Muscle Mass

The invention relates to a FGF19 polypeptide for its use in the prevention and/or treatment of loss of muscle in a mammal body, wherein it induces an increase of muscle mass in said mammal body. In other terms, a development of muscle mass in the mammal body is observed.

According to this embodiment of the invention, the FGF19 is used as an agent increasing muscle fibers size for increasing the muscle mass and/or lean mass in a mammal body.

As already described, FGF19 prevents muscle atrophy. However, FGF19 polypeptide might also be used in non-therapeutic uses. Indeed, FGF19 also induces a development of muscle mass in the treated mammal body, this muscular development being linked to the increase of the muscle fibers size.

This non-therapeutic use of FGF19, as an agent increasing muscle fibers size, is mainly dedicated to athletes and to space travelers. In particular, it is understood that the population concerned with this non-therapeutic use is composed of individuals that do not suffer of muscle atrophy.

Therefore, the present application also concerns the use of a FGF19 polypeptide as an agent increasing muscle fibers size, for the development or the maintenance of muscle mass in a mammal body, in particular in a healthy mammal body, more particularly in a mammal body that does not suffer and/or is not at risk of muscle atrophy. The invention is also related to a method for increasing the muscle mass and/or the lean mass of a mammal body, comprising the administration to said body of an efficient amount of a FGF19 polypeptide.

Preferentially, the invention concerns a method for increasing the muscle mass and/or the lean mass of a mammal body, comprising the oral administration to said body of an efficient amount of a FGF19 polypeptide.

More preferentially, the invention concerns a method for increasing the muscle mass and/or the lean mass of an individual, comprising the oral administration to said individual of an efficient amount of a FGF19 polypeptide.

According to the method for increasing the muscle mass and/or the lean mass described herein, a FGF19 polypeptide is used as an agent increasing muscle fibers size.

The increase in the muscle mass, or development of muscle mass, can be sudden or progressive. The increase of muscle mass can be voluntary or involuntary. In a specific aspect of the invention, the increase of muscle mass is voluntary. Such development of muscle mass can be localized in a specific body area or can be uniform through the body.

The percentage of increase/development of muscle mass can be measured in percentages of increase compared to the muscle mass observed at a precedent moment (To), in particular before the first administration of the FGF19 polypeptide. For example, the increase of muscle mass is an increase of at least 1%, 2%, 3%, 4%, 5%, 6%, 7%, 8%, 9%, 10%, 15%, 20%, 25%, 30%, 35%, 40% or even 45% of the total muscle mass of the body as measured in said precedent moment.

According to this invention, an increase of muscle mass corresponds to an increase of lean body mass, as presented above.

According to an embodiment of the invention, the increase of muscle mass corresponds to an increase of the lean body mass, the lean body mass being measured at a time point $T_0$ before the first administration of the FGF19 polypeptide, and then at a time point $T_1$, the period between $T_0$ and $T_1$ being a significant period of time of about two days, three days, four days, five days, six days, a week, two weeks, three weeks, four weeks, a month, two months, three months, four months, five months, six months, seven months, eight months, nine months, ten months, eleven months, twelve months, fifteen months, eighteen months, two years, three years, four years, or five years.

In a specific aspect of the invention, the FGF19 polypeptide is used as an agent increasing muscle fibers size for increasing the muscle mass in a non-human mammal body.

It is an important goal of livestock producers to optimize efficiency of feed conversion of the feedlot diet into edible human food products of high quality, without posing any significant risk to the consumer.

In the area of food production, this specific use of FGF19 polypeptide is useful for increasing the muscle mass and/or lean mass of livestock, in order to improve the meat production.

According to this embodiment of the invention, the non-human mammal is preferably chosen among cattle, pigs, sheeps, goats and other animals whose meat is usually consummated.

According to another embodiment of the invention, the FGF19 polypeptide is used as an agent increasing muscle fibers size for increasing the muscle mass and/or lean mass in a human body.

A large population of persons wishes to aesthetically add muscle to body mass, or to increase strength in order to reduce fatigue stamina and/or appearance.

A method for increasing the muscle mass and/or the lean mass of an human body, comprising the administration to said human body of an efficient amount of FGF19 polypeptide, is another embodiment of the invention.

According to another embodiment of the invention, when the FGF19 is used as an agent increasing muscle fibers size, the strength of at least one muscle in the treated body is optimized.

The strength of any given muscle depends upon different factors and notably of the size of the muscle fibers. As shown in examples 6 and 7, concomitantly with the increase of the muscle fibers size, the grip strength of FGF19-treated mice is significantly increased (at least 10% of increase) after fourteen days of treatment.

Therefore, the present application also concerns the use of a FGF19 polypeptide as an agent increasing muscle fibers size, for optimizing the strength of at least one muscle in a mammal body, in particular in a healthy mammal body, more particularly in a mammal body that does not suffer and/or is not at risk of muscle atrophy.

This non-therapeutic use of FGF19, as an agent increasing muscle fibers size, and therefore as an agent increasing the strength of at least one muscle in the body, is mainly dedicated to the population of athletes.

Muscles that can be targeted for the non-therapeutic uses of FGF19 are in particular the skeletal muscles, used to effect skeletal movement such as locomotion and in maintaining posture.

Administration of the Polypeptide

The term "administration" means the introduction of the polypeptide into the body of a mammal animal or a human being.

The polypeptide can be administered by any route of administration. Suitable routes may include oral, buccal, by inhalation spray, sublingual, rectal, transdermal, vaginal, transmucosal, nasal or intestinal administration, parenteral delivery, including intramuscular, subcutaneous and intravenous injections, or other modes of delivery.

A preferred mode of administration is the intramuscular administration of the polypeptide to the mammal body. Preferably, the polypeptide is injected into the target muscle whose mass is reduced or should be increased.

Another preferred mode of administration is the intravenous administration of the FGF19 polypeptide to the mammal body.

Another mode of administration is the oral administration, the FGF19 polypeptide being formulated into a pharmaceutical vehicle allowing its biological activity to be conserved up to the target tissues of the treated body.

The oral route and intravenous route are the preferred routes of administration when the loss of muscle mass is generalized in the body.

The oral route is a preferred route of administration when an increase of muscle mass is desirable for non-therapeutic purposes.

In a specific embodiment of the invention, the administration of the FGF19 polypeptide is performed on a daily basis, for at least three days. In particular, the administration of the FGF19 polypeptide is realized daily, for at least three days, four days, five days, six days, seven days, ten days, fourteen days or two weeks, three weeks, four weeks, five weeks, or six weeks.

The "effective amount" of the polypeptide refers to the amount necessary to elicit the desired biological response. As can be appreciated by the man skilled in the art, the effective amount may vary depending on factors such as the desired biological endpoint, depending on the effect to achieve.

Typical dose ranges are from about 1 µg/kg to about 1 g/kg of body weight per day; a preferred dose range is from about 0.01 mg/kg to 100 mg/kg of body weight per day. A preferred dose is comprised in a dose range of 0.05 mg/kg to 10 mg/kg.

Pharmaceutical Compositions

The present invention also relates to a pharmaceutical composition comprising at least a FGF19 polypeptide and a pharmaceutical vehicle, for its use in the prevention and/or treatment of loss of muscle mass in a mammal body.

As previously disclosed, the FGF19 polypeptide is used as an agent increasing muscle fibers size.

A pharmaceutically vehicle is a physiologically acceptable vehicle prepared with nontoxic components, useful for administering an active compound to an animal or a human body. Various aqueous carriers may be used, for example water, saline buffer solution, a glycine solution 0.4% or 0.3%, or hyaluronic acid solution.

The pharmaceutical composition may be sterilized by any known conventional method, such as filtration. The resulting aqueous solution may be packaged for use, or can be lyophilized. A lyophilized preparation can be combined with a sterile solution before use.

The pharmaceutical composition of the invention may include any pharmaceutically acceptable excipient required to approximate physiological conditions, such as buffering agents, agents for pH adjustment, for isotonicity adjustment, and wetting agents. Such preparations may also include antioxidants, preservatives, and/or adjuvants.

Methods of administration of the pharmaceutical composition include, but are not limited to, intradermal, intramuscular, intraperitoneal, intravenous, subcutaneous, intranasal, epidural, and oral routes. The compositions may be administered by any convenient route, for example by infusion or bolus injection, by absorption through epithelial or mucocutaneous linings (e.g., oral mucosa, rectal and intestinal mucosa, etc.).

Preferred modes of administration are the intramuscular administration of the pharmaceutical composition to the mammal body, in particular into the target muscle whose mass is reduced or should be increased, and oral administration.

According to a specific embodiment, the pharmaceutical composition for its use in the prevention and/or treatment of loss of muscle mass, comprises at least one another active principle.

In a first embodiment, the loss of muscle mass is due to a specific medical condition, and the other active principle is a drug for treating said specific medical condition.

In particular, said drug can be a drug for treating cachexia, such as megestrol acetate, medroxyprogesterone, ghrelin, omega-3-fatty acid, and other drugs presented in the review from (Aoyagi et al., 2015).

In a second embodiment, an increase of the muscle mass of animals, in particular cattle, is desirable for improving the meat production; in this case, the other active principle is chosen, in a non-limitative manner, among hormones, growth factors, adrenergic β-agonist compounds and medicated feed additives.

In a third embodiment, an increase of the muscle mass is desirable for athletical purposes, and the other active principle is a performance-enhancing drug.

In a non-limitative manner, said performance-enhancing drug can be chosen among phenylpropanolamine, amphetamine, ephedrine, tyrosine or a tyrosine precursor, or erythropoietin.

Other active principles can advantageously be added into the composition of the invention. These compounds are chosen among the following non-exhaustive list:

Nutritional supplements, in particular supplements with high protein content,

Solutions of amino acids, in particular adapted for the needs of human or animal bodies, and Protein hydrolysates, whose consumption allows amino acids to be absorbed by the body more rapidly than intact proteins, thus maximizing nutrient delivery to muscle tissues.

Therefore, the pharmaceutical composition for its use according to the invention may comprise another active principle, selected among the following compounds: a drug for treating cachexia, a performance-enhancing drug, a nutritional supplement, a solution of amino acids or of protein hydrolysates.

EXAMPLES

Material and Methods

Animal Experiments

All animal experiments were approved by the Norwegian State Board of Biological Experiments with Living Animals. Nr1i2$^{+/+}$ and Nr1i2$^{-/-}$ mice were maintained in a 12956/SvEvTac background and housed (n=4-6 mice/cage) in a ventilated rodent housing system with a controlled temperature (22° C.-23° C.) and free access to food and water.

Mice were fed a low-fat diet (chow) that contained 12% of calories from fat, 27% from protein, and 61% from carbohydrates (Special Diets Services, Essex, England). Body weight was recorded weekly and food intake was measured over 5 to 7 days. At the end of the protocols, mice were anaesthetized with isoflurane and sacrificed by heart puncture. Blood was collected in EDTA-coated tubes and tissues were dissected, weighed, and either dipped in liquid nitrogen or fixed for histochemistry investigations.

For studying the in vivo effect of FGF19 treatment, single-housed young (3 week-old) and adult (18 week-old) mice were daily treated with human recombinant FGF19 (R&D Systems, UK) administrated subcutaneously (0.1 mg/kg) in a PBS/0.1% BSA solution (vehicle) for 7 days.

Gene Expression

Tissue RNA was extracted using Trizol and levels of specific mRNA were quantified using real-time PCR.

Immunohistochemistry

Following harvest, mouse skeletal muscles were immediately embedded in OCT and frozen in liquid nitrogen. Cross-sections (10 µm) from the mid-belly were stained with myosin adenosine triphosphatase (ATPase) to determine type I (slow-twitch) and type II (fast-twitch) fibers. For muscle fiber area analyses, transversal cross-sections were immunolabeled with anti-Laminin antibody (L9393, Sigma) to determine the muscle fiber size distribution and total number of fibers. Pictures were acquired using an AxioCam camera (Zeiss, Germany) and examined using digital image software (Automeasure, Zeiss, Germany). At least 250 fibers were analyzed for each muscle sample.

Ex Vivo Experiments

Once anesthetised, the small intestine of overnight fasted $Nrli2^{+/+}$ and $Nrli2^{-/-}$ mice was isolated and a segment of approximately 1 cm was collected from the distal part of the ileum, quickly washed and incubated for 2.5 h at 37° C. in 1 mL of high-glucose DMEM with glutamine and pyruvate, supplemented with 10% calf serum, 100 U/ml penicillin and 100 U/ml streptomycin.

FGF19 Treatment of Human Skeletal Muscle Cells

For the study of human primary myotubes, muscle biopsies were taken from healthy lean subjects. All participants gave their written consent after being informed of the nature, purpose and possible risks of the study. The experimental protocol (agreement number 2012-111/A13-06) was approved by the Ethical Committees Sud-EST IV and performed according to the French legislation (Huriet law).

Human myoblasts were cultured and differentiated as known by the man skilled in the art. Briefly, myoblasts were established from muscle satellite cells and proliferated in HAM-F10 medium (Gibco, Life Technologies, Grand Island, N.Y., USA) supplemented with 20% fetal bovine serum (FBS) (Gibco). After reaching confluence, myoblasts were differentiated into myotubes during 7-10 days in DMEM supplemented with 2% FBS. Muscle cell differentiation was characterized by the fusion of myoblasts into polynucleated myotubes. Differentiated myotubes were treated with human recombinant FGF19 (R&D Systems, UK) as indicated. Measurement of the area of immunofluorescence-labeled myotubes was performed.

Statistics

Results are presented as means±SEM. Data were analyzed by two tailed Mann-Whitney test. Statistical analysis of fiber cross-sectional area distribution was performed using the chi2 test. Statistical significance was set at $P<0.05$.

Example 1. $Nrli2^{-/-}$ Mice are a Relevant Model for Studying the Effects of Increased Plasmatic Concentrations of FGF15

Figure 1:
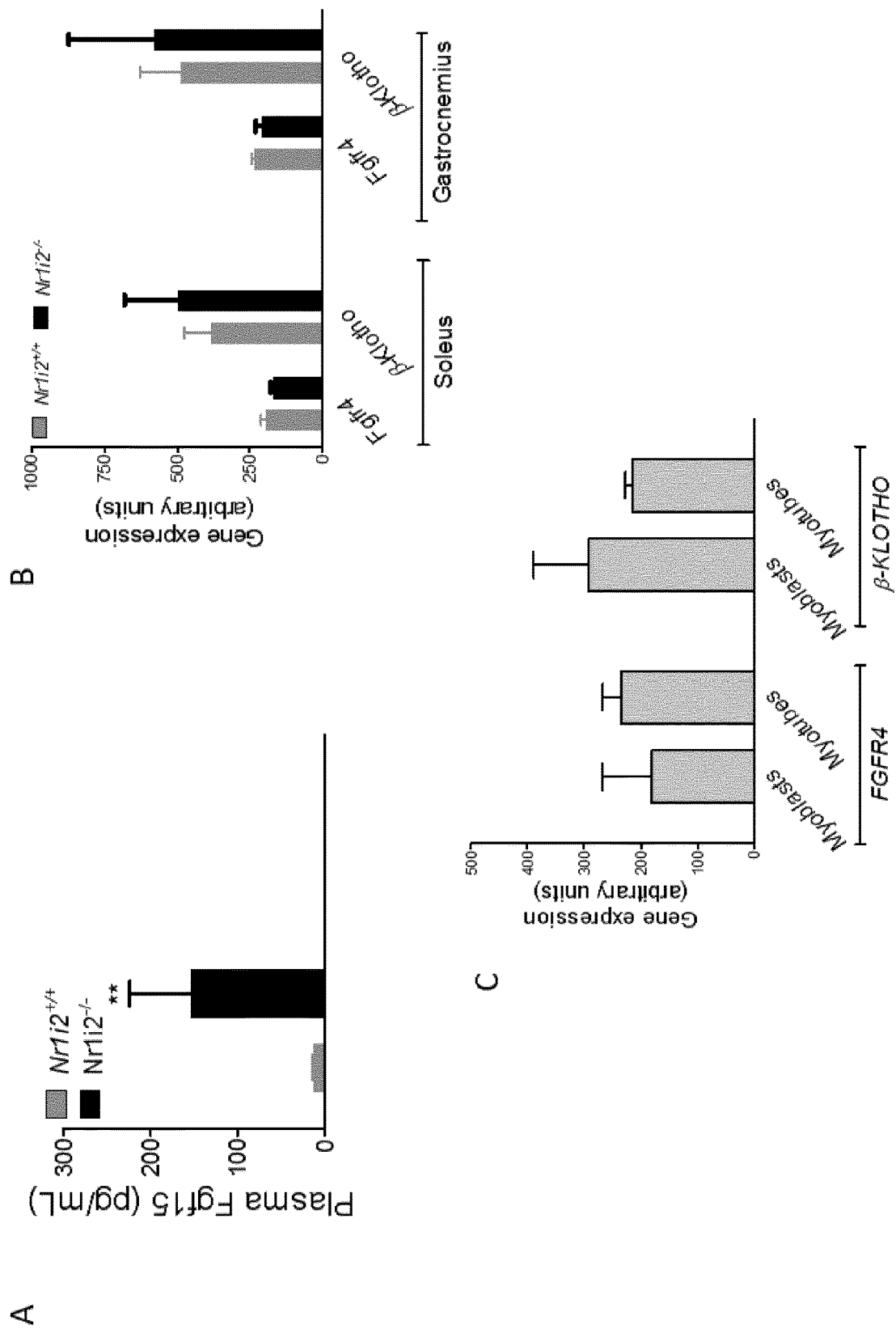
FIG. 1. Expression of FGF15 in Nr1i2$^{-/-}$ mice, and of FGF receptors in mice and human cells (A) Plasma concentration levels of FGF15 in Nr1i2$^{+/+}$ (in grey, left column) and Nr1i2$^{-/-}$ (in black, right column) mice (n=10-12).

There is a 8-fold increase in circulating Fgf15 levels in $Nrli2^{-/-}$ mice as compared to $Nrli2^{+/+}$ mice (FIG. 1A).

Circulating levels of FGF19 fluctuate according to food intake. To verify that the elevated plasma levels of Fgf15 observed in $Nrli2^{-/-}$ mice were not a consequence of their increased food intake, we harvested the ileum of overnight-fasted animals and incubated these explants for 2.5 h. In this experimental setting, only ileal explants from $Nrli2^{-/-}$ mice expressed Fgf15, resulting in higher concentrations of FGF15 in the medium (Results not shown).

FGF19 is known to act through a specific receptor (FGFR4), which requires the co-receptor ß-Klotho for full action. We confirmed that both FGFR4 and β-KLOTHO genes were expressed in mouse muscle and human skeletal muscle cells (FIG. 1B, 1C).

Example 2. High Circulating Levels of FGF15 are Associated with Skeletal Muscle Hypertrophy in $Nrli2^{-/-}$ Mice As compared to $Nrli2^{+/+}$ muscles, the weight of skeletal muscles was markedly enhanced for all studied muscles (soleus, tibialis and gastrocnemius) of $Nrli2^{-/-}$ mice and this result was found both in young adult (22 weeks-old, FIG. 2A) and in aged mice (17 months-old, FIG. 2B).

Example 3. High Circulating Levels of FGF15 are Associated with Significant Increase in the Size of Muscular Fibers in in $Nrli2^{-/-}$ Mice The number of fibers of different sizes is measured from laminin stained muscles. Fibers are classified in 13 "area classes", from a fiber area inferior to 600 µm$^2$ to a fiber area superior to 6000 µm$^2$.

Fibers having a surface superior to 1500 µm$^2$ are more frequently observed in $Nrli2^{-/-}$ mice, compared to $Nrli2^{+/+}$ mice (FIG. 3A, 3B).

These results show that, as compared to $Nrli2^{+/+}$ mice, the area of the muscle fibers is markedly increased both in soleus (FIG. 3A) and in tibialis (FIG. 3B) of $Nrli2^{-/-}$ mice.

Example 4. In Vitro Results on Human Muscle Cells

To explore the direct role of FGF15/19 on skeletal muscle, the effects of FGF19 in vitro in primary human muscle cells were investigated.

When FGF19 is added at both physiological and pharmacological doses during the differentiation process of myoblasts to myotubes, or directly to myotubes, the area of the resulting myotubes is significantly enhanced (FIG. 4A)

FIG. 4B shows images of the myosine staining of myotubes, allowing the estimation of the myotube area.

Example 5. In Vivo Results Obtained on Mice after Injection of FGF19

To validate in vivo the role of FGF15/19 in muscle mass development, we treated normal control mice with a daily injection of recombinant human FGF19, which is biologically active in mice and more stable than its murine counterpart Fgf15.

One hour after subcutaneous injection, plasma levels of FGF19 increased to 17.8±1.2 ng/ml in FGF19-treated mice whereas plasma FGF19 was not detectable in vehicle-treated mice (not shown).

In FIG. 5, white bars show the results obtained without FGF19 treatment, grey bars show the results obtained in FGF-19 treated mice.

After seven days, body weight gain and food intake of FGF19- and vehicle-treated mice were similar (results not shown), but compared to vehicle-treated mice, mice receiving FGF19 showed a significant enlargement of the size of the soleus fibers (FIG. 5) both in young (3 week-old, FIG. 5A) and in adult (18 week-old, FIG. 5A'") mice. The weights of the measured muscles (soleus and gastrocnemius) were significantly increased after daily treatment with FGF19 both in young (3 weeks-old) and in adult (18 weeks-old) mice (FIG. 5 B).

FIG. 5C shows the mean soleus fiber area after seven days of FGF19 treatment: in young mice, the mean area doubles; in adults, a significant increasing in size fiber (11.9% compared to the mean area of untreated mice) is also notified.

Example 6. In Vivo Results Obtained on Animal Model of Dexamethasone-Induced Muscle Atrophy C57BL/6 mice (23-week-old) were treated with dexamethasone (25 mg/kg) and dexamethasone plus FGF19 (0.1 mg/kg) for 14 days. As negative controls, mice were treated with a pharmaceutically acceptable excipient designated as "vehicle".

White bars represent the results obtained in vehicle-treated mice, grey bars represent the results obtained in dexamethasone-treated mice, and stripped bars represent the results obtained with dexamethasone and FGF19-treated mice. Distributions are analyzed using Kolmogorov-Smirnov test with P<0.01.

As it is well known by the man skilled in the art, dexamethasone-treatment induces a state of muscle atrophy (Gilson et al.).

After fourteen days of treatment, the muscle weight (FIG. 6A), the size of tibialis muscle fibers (FIG. 6B), the mean fiber area (FIG. 6C) and the grip strength (FIG. 6D) of the mice are evaluated.

Evaluation of the grip strength is realized as described below: Muscle strength was recorded using a GT3 grip test meter system (Bioseb, Vitrolles, France). Mice were allowed to hold a metal grid with four paws and were gently pulled backwards by the tail until the animals could no longer hold the grid. Each mouse was given 4 trials and average values were used to represent the muscle grip strength of an individual mouse. Investigator was blinded to the animal group treatments.

FIG. 6 shows that:

As expected, in dexamethasone-treated mice, the weight of both muscles, soleus and tibialis, is significantly decreased; the size of the tibialis muscle fibers is reduced (FIGS. 6B and 6C); and the grip strength of mice is lowered.

Importantly, when mice are concomitantly treated with FGF19 (0.1 mg/kg), the dexamethasone-induced decrease of muscle weight, size of muscle fibers and grip strength of mice, is attenuated, and for some effects is completely abolished; the muscle weight of soleus and the grip strength are even increased compared to the control situation.

Example 7. In Vivo Results Obtained on Animal Models of Obesity-Induced Muscle Atrophy ob/ob mice (13-week-old), an animal model for obesity, were daily treated with FGF19 (0.1 mg/kg) for 7 days. Negative controls are ob/+ mice (non obese) and ob/ob mice treated with the vehicle.

White bars represent the results obtained in ob/+ mice, grey bars represent the results obtained in vehicle-treated mice, and stripped bars represent the results obtained with FGF19-treated ob/ob mice. Distributions are analyzed using Kolmogorov-Smirnov test with P<0.01.

As it is well known by the man skilled in the art, obesity induces a loss of muscle mass, as well as a decrease in size fibers.

After seven days of treatment, the muscle weight (FIG. 7A), the size of tibialis muscle fibers (FIG. 7B), the mean fiber area (FIG. 7C) and the grip strength (FIG. 7D) of the mice are evaluated.

FIG. 7 shows that:

As expected, in ob/ob mice, the weight of both muscles, soleus and tibialis, is significantly decreased when compared to ob/+ mice; the size of the tibialis muscle fibers is reduced (FIGS. 7B and 7C), in particular fibers showing a size superior to 3200 $\mu m^2$ are absent in these mice; and the grip strength of mice is dramatically lowered.

Importantly, when ob/ob mice are treated with FGF19 (0.1 mg/kg) for seven days, the muscle weight, size of muscle fibers and grip strength of mice are increased. The muscle weight of both soleus and tibialis is superior than in non-treated ob/ob mice; the mean fiber area is increased, from 1250 $\mu m^2$ in ob/ob mice to about 1350 $\mu m^2$ in ob/ob FGF19-treated mice (FIG. 7C); and the grip strength is improved.

In conclusion, these results show that FGF19 polypeptide can be used as an agent increasing muscle fibers size, in the prevention (see example 6) and treatment (see example 7) of loss of muscle mass in a mammal body.

REFERENCES

Aoyagi T, Terracina K P, Raza A, Matsubara H, Takabe K. *Cancer cachexia, mechanism and treatment.* World J Gastrointest Oncol. 2015 Apr. 15; 7(4):17-29.

Fu L, John L M, Adams S H, Yu X X, Tomlinson E, Renz M, Williams P M, Soriano R, Corpuz R, Moffat B, Vandlen R, Simmons L, Foster J, Stephan J P, Tsai S P, Stewart T A. *Fibroblast growth factor 19 increases metabolic rate and reverses dietary and leptin-deficient diabetes.* Endocrinology. 2004 June; 145(6):2594-603. Epub 2004 Feb. 19.

Kir S, Beddow S A, Samuel V T, Miller P, Previs S F, Suino-Powell K, Xu H E, Shulman G I, Kliewer S A, Mangelsdorf D J. *FGF19 as a postprandial, insulin-independent activator of hepatic protein and glycogen synthesis.* Science. 2011 Mar. 25; 331(6024):1621-4.

Potthoff M J, Boney-Montoya J, Choi M, He T, Sunny N E, Satapati S, Suino-Powell K, Xu H E, Gerard R D, Finck B N, Burgess S C, Mangelsdorf D J, Kliewer S A. *FGF15/19 regulates hepatic glucose metabolism by inhibiting the CREB-PGC-1α pathway.* Cell Metab. 2011 Jun. 8; 13(6):729-38. doi: 10.1016/j.cmet.2011.03.019.

Lin B C, Wang M, Blackmore C, Desnoyers L R. *Liver-specific activities of FGF19 require Klotho beta.* J Biol Chem. 2007 Sep. 14; 282(37):27277-84. Epub 2007 Jul. 11.

Yousef H, Conboy M J, Mamiya H, Zeiderman M, Schlesinger C, Schaffer D V S, Conboy I M. *Mechanisms of action of hESC-secreted proteins that enhance human and mouse myogenesis.* Aging (Albany N.Y.). 2014 August; 6(8):602-20.

Gilson H. et al. *Myostatin gene deletion prevents glucocorticoid-induced muscle atrophy.* Endocrinology 148, 452-460 (2007).

The invention claimed is:

1. A method for increasing the muscle fiber size in a mammal wherein the mammal has muscle atrophy, said method comprising administering an effective amount of a fibroblast growth factor 19 (FGF19) polypeptide to the mammal.

2. The method according to claim 1, wherein the mammal is a human.

3. The method according to claim 1, wherein an increase in muscle mass in the mammal is observed.

4. The method according to claim 1, wherein the mammal is not a human.

5. The method according to claim 1, wherein muscle strength is increased in the mammal.

6. The method according to claim 1, wherein the FGF19 polypeptide has an amino acid sequence selected from the group consisting of SEQ ID NO:1-10.

7. The method according to claim 1, wherein the muscle atrophy is caused by cachexia.

8. The method according to claim 1, wherein the muscle atrophy is caused by sarcopenia.

9. The method according to claim 1, wherein the muscle atrophy is caused by prolonged immobilization.

10. The method according to claim 1, wherein the muscle atrophy is caused by obesity.

11. The method according to claim 1, wherein the mammal is a bovine.

12. A method for increasing the muscle fiber size in a mammal wherein the mammal has muscle atrophy, said method comprising administering an effective amount of a pharmaceutical composition comprising and FGF19 polypeptide and a pharmaceutically-acceptable vehicle to the mammal.

13. The method according to claim 12, wherein the pharmaceutical composition further comprises a drug for treating cachexia, a performance-enhancing drug, a nutritional supplement, a solution of amino acids, or protein hydrolysates.

* * * * *

SEQUENCE LISTING

<160> NUMBER OF SEQ ID NOS: 10

<210> SEQ ID NO 1
<211> LENGTH: 216
<212> TYPE: PRT
<213> ORGANISM: Homo sapiens

<400> SEQUENCE: 1

Met Arg Ser Gly Cys Val Val His Val Trp Ile Leu Ala Gly Leu
1               5                   10                  15

Trp Leu Ala Val Ala Gly Arg Pro Leu Ala Phe Ser Asp Ala Gly Pro
            20                  25                  30

His Val His Tyr Gly Trp Gly Asp Pro Ile Arg Leu Arg His Leu Tyr
            35                  40                  45

Thr Ser Gly Pro His Gly Leu Ser Ser Cys Phe Leu Arg Ile Arg Ala
        50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
                100                 105                 110

Leu Gln Tyr Ser Glu Glu Asp Cys Ala Phe Glu Glu Ile Arg Pro
            115                 120                 125

Asp Gly Tyr Asn Val Tyr Arg Ser Glu Lys His Arg Leu Pro Val Ser
            130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Gly His Leu Glu Ser Asp Met Phe Ser Ser Pro Leu
            180                 185                 190

Glu Thr Asp Ser Met Asp Pro Phe Gly Leu Val Thr Gly Leu Glu Ala
            195                 200                 205

Val Arg Ser Pro Ser Phe Glu Lys
    210                 215

<210> SEQ ID NO 2
<211> LENGTH: 220
<212> TYPE: PRT
<213> ORGANISM: Sus scrofa

<400> SEQUENCE: 2

Ala Met Arg Ser Ala Pro Ser Arg Cys Ala Val Val Arg Ala Leu Val
1               5                   10                  15

Leu Ala Gly Leu Trp Leu Ala Ala Gly Arg Pro Leu Ala Phe Ser
            20                  25                  30

Asp Ala Gly Pro His Val His Tyr Gly Trp Gly Glu Ser Val Arg Leu
            35                  40                  45

Arg His Leu Tyr Thr Ala Ser Pro His Gly Val Ser Ser Cys Phe Leu
        50                  55                  60

Arg Ile His Ser Asp Gly Pro Val Asp Cys Ala Pro Gly Gln Ser Ala
65                  70                  75                  80

His Ser Leu Met Glu Ile Arg Ala Val Ala Leu Ser Thr Val Ala Ile
                85                  90                  95

Lys Gly Glu Arg Ser Gly Arg Tyr Leu Cys Met Gly Ala Asp Gly Lys

```
            100                 105                 110
Met Gln Gly Gln Thr Gln Tyr Ser Asp Glu Asp Cys Ala Phe Glu Glu
                115                 120                 125

Glu Ile Arg Pro Asp Gly Tyr Asn Val Tyr Trp Ser Lys Lys His His
    130                 135                 140

Leu Pro Val Ser Leu Ser Ser Ala Arg Gln Arg Gln Leu Tyr Lys Gly
145                 150                 155                 160

Arg Gly Phe Leu Pro Leu Ser His Phe Leu Pro Met Leu Ser Thr Leu
                165                 170                 175

Pro Ala Glu Pro Glu Asp Leu Gln Asp Pro Phe Lys Ser Asp Leu Phe
                180                 185                 190

Ser Leu Pro Leu Glu Thr Asp Ser Met Asp Pro Phe Arg Ile Ala Ala
                195                 200                 205

Lys Leu Gly Ala Val Lys Ser Pro Ser Phe Tyr Lys
210                 215                 220

<210> SEQ ID NO 3
<211> LENGTH: 218
<212> TYPE: PRT
<213> ORGANISM: bos taurus

<400> SEQUENCE: 3

Met Arg Ser Ala Pro Ser Arg Cys Ala Val Ala Arg Ala Leu Val Leu
1               5                   10                  15

Ala Gly Leu Trp Leu Ala Ala Gly Arg Pro Leu Ala Phe Ser Asp
                20                  25                  30

Ala Gly Pro His Val His Tyr Gly Trp Gly Ser Val Arg Leu Arg
                35                  40                  45

His Leu Tyr Thr Ala Gly Pro Gln Gly Leu Tyr Ser Cys Phe Leu Arg
    50                  55                  60

Ile His Ser Asp Gly Ala Val Asp Cys Ala Gln Val Gln Ser Ala His
65                  70                  75                  80

Ser Leu Met Glu Ile Arg Ala Val Ala Leu Ser Thr Val Ala Ile Lys
                85                  90                  95

Gly Glu Arg Ser Val Leu Tyr Leu Cys Met Asp Ala Asp Gly Lys Met
                100                 105                 110

Gln Gly Leu Thr Gln Tyr Ser Ala Glu Asp Cys Ala Phe Glu Glu Glu
                115                 120                 125

Ile Arg Pro Asp Gly Tyr Asn Val Tyr Trp Ser Arg Lys His His Leu
    130                 135                 140

Pro Val Ser Leu Ser Ser Arg Gln Arg Gln Leu Phe Lys Ser Arg
145                 150                 155                 160

Gly Phe Leu Pro Leu Ser His Phe Leu Pro Met Leu Ser Thr Ile Pro
                165                 170                 175

Ala Glu Pro Glu Asp Leu Gln Glu Pro Leu Lys Pro Asp Phe Phe Leu
                180                 185                 190

Pro Leu Lys Thr Asp Ser Met Asp Pro Phe Gly Leu Ala Thr Lys Leu
                195                 200                 205

Gly Ser Val Lys Ser Pro Ser Phe Tyr Asn
210                 215

<210> SEQ ID NO 4
<211> LENGTH: 94
<212> TYPE: PRT
<213> ORGANISM: Equus caballus
```

<400> SEQUENCE: 4

```
Ala Ala Gly Arg Pro Leu Ala Leu Ser Asp Ala Gly Pro His Val His
1               5                   10                  15

Tyr Gly Trp Gly Glu Pro Ile Arg Leu Arg His Leu Tyr Thr Ala Gly
                20                  25                  30

Pro His Gly Leu Ser Ser Cys Phe Leu Arg Ile Arg Ala Asp Gly Ala
            35                  40                  45

Val Asp Cys Ala Arg Gly Gln Ser Ala His Ser Leu Val Glu Ile Arg
50                  55                  60

Ala Val Ala Leu Arg Thr Val Ala Ile Lys Gly Val His Ser Val Arg
65                  70                  75                  80

Tyr Leu Cys Met Gly Ala Asp Gly Arg Met Gln Gly Leu Val
                85                  90
```

<210> SEQ ID NO 5
<211> LENGTH: 137
<212> TYPE: PRT
<213> ORGANISM: Ovis aries

<400> SEQUENCE: 5

```
Leu Met Glu Ile Arg Ala Val Ala Leu Ser Thr Val Ala Ile Lys Gly
1               5                   10                  15

Glu Arg Ser Val Leu Phe Leu Cys Met Asp Ala Asp Gly Lys Met Gln
                20                  25                  30

Gly Leu Thr Gln Tyr Ser Ala Glu Asp Cys Ala Phe Glu Glu Glu Ile
            35                  40                  45

Arg Pro Asp Gly Tyr Asn Val Tyr Trp Ser Arg Lys His His Leu Pro
50                  55                  60

Val Ser Leu Ser Ser Arg Gln Arg Gln Leu Phe Lys Ser Arg Gly
65                  70                  75                  80

Phe Leu Pro Leu Ser His Phe Leu Pro Met Leu Ser Thr Ile Pro Ala
                85                  90                  95

Glu Pro Glu Asp Leu Gln Glu Pro Leu Lys Pro Asp Phe Phe Leu Pro
                100                 105                 110

Leu Lys Thr Asp Ser Met Asp Pro Phe Gly Leu Ala Thr Lys Leu Gly
            115                 120                 125

Ser Val Lys Ser Pro Ser Phe Tyr Thr
        130                 135
```

<210> SEQ ID NO 6
<211> LENGTH: 193
<212> TYPE: PRT
<213> ORGANISM: canis familiairis

<400> SEQUENCE: 6

```
Pro Leu Ala Phe Ser Asp Ala Gly Pro His Val His Ser Phe Trp Gly
1               5                   10                  15

Glu Pro Ile Arg Leu Arg His Leu Tyr Thr Ala Gly Pro His Gly Leu
                20                  25                  30

Ser Ser Cys Phe Leu Arg Ile Arg Ala Asp Gly Gly Val Asp Cys Ala
            35                  40                  45

Arg Gly Gln Ser Ala His Ser Leu Met Glu Met Arg Ala Val Ala Leu
50                  55                  60

Arg Thr Val Ala Ile Lys Gly Val His Ser Gly Arg Tyr Leu Cys Met
65                  70                  75                  80

Gly Ala Asp Gly Arg Met Gln Gly Leu Pro Gln Tyr Ser Ala Gly Asp
```

```
                85                  90                  95

Cys Thr Phe Glu Glu Ile Arg Pro Asp Gly Tyr Asn Val Tyr Trp
            100                 105                 110

Ser Lys Lys His His Leu Pro Ile Ser Leu Ser Ser Ala Lys Gln Arg
        115                 120                 125

Gln Leu Tyr Lys Gly Arg Gly Phe Leu Pro Leu Ser His Phe Leu Pro
    130                 135                 140

Ile Leu Pro Gly Ser Pro Thr Glu Pro Arg Asp Leu Glu Asp His Val
145                 150                 155                 160

Glu Ser Asp Gly Phe Ser Ala Ser Leu Glu Thr Asp Ser Met Asp Pro
                165                 170                 175

Phe Gly Ile Ala Thr Lys Ile Gly Leu Val Lys Ser Pro Ser Phe Gln
            180                 185                 190

Lys

<210> SEQ ID NO 7
<211> LENGTH: 219
<212> TYPE: PRT
<213> ORGANISM: Felis catus

<400> SEQUENCE: 7

Met Arg Ser Ala Pro Ser Gln Cys Ala Val Thr Arg Ala Leu Val Leu
1               5                   10                  15

Ala Gly Leu Trp Leu Ala Ala Gly Arg Pro Leu Ala Phe Ser Asp
            20                  25                  30

Ala Gly Pro His Val His Tyr Gly Trp Gly Glu Pro Ile Arg Leu Arg
        35                  40                  45

His Leu Tyr Thr Ala Gly Pro His Gly Leu Ser Ser Cys Phe Leu Arg
    50                  55                  60

Ile Arg Ala Asp Gly Gly Val Asp Cys Ala Arg Ser Gln Ser Ala His
65                  70                  75                  80

Ser Leu Val Glu Ile Arg Ala Val Ala Leu Arg Thr Val Ala Ile Lys
                85                  90                  95

Gly Val His Ser Val Arg Tyr Leu Cys Met Gly Ala Asp Gly Arg Met
            100                 105                 110

Gln Gly Leu Leu Gln Tyr Ser Ala Gly Asp Cys Ala Phe Gln Glu Glu
        115                 120                 125

Ile Arg Pro Asp Gly Tyr Asn Val Tyr Arg Ser Glu Lys His Arg Leu
    130                 135                 140

Pro Val Ser Leu Ser Ser Ala Ile Gln Arg Gln Leu Tyr Lys Gly Arg
145                 150                 155                 160

Gly Phe Leu Pro Leu Ser His Phe Leu Pro Met Leu Pro Gly Ser Pro
                165                 170                 175

Ala Glu Pro Arg Asp Leu Gln Asp His Val Glu Ser Glu Arg Phe Ser
            180                 185                 190

Ser Pro Leu Glu Thr Asp Ser Met Asp Pro Phe Gly Ile Ala Thr Lys
        195                 200                 205

Met Gly Leu Val Lys Ser Pro Ser Phe Gln Lys
    210                 215

<210> SEQ ID NO 8
<211> LENGTH: 218
<212> TYPE: PRT
<213> ORGANISM: Oryctolagus cuniculus

<400> SEQUENCE: 8
```

Met Arg Arg Ala Pro Ser Gly Ala Ala Arg Ala Leu Val Leu
1               5                   10                  15

Ala Gly Leu Trp Leu Ala Ala Ala Arg Pro Leu Ala Leu Ser Asp
            20                  25                  30

Ala Gly Pro His Leu His Tyr Gly Trp Gly Glu Pro Val Arg Leu Arg
            35                  40                  45

His Leu Tyr Ala Thr Ser Ala His Gly Val Ser His Cys Phe Leu Arg
    50                  55                  60

Ile Arg Ala Asp Gly Ala Val Asp Cys Glu Arg Ser Gln Ser Ala His
65                  70                  75                  80

Ser Leu Leu Glu Ile Arg Ala Val Ala Leu Arg Thr Val Ala Phe Lys
                85                  90                  95

Gly Val His Ser Ser Arg Tyr Leu Cys Met Gly Ala Asp Gly Arg Met
                100                 105                 110

Arg Gly Gln Leu Gln Tyr Ser Glu Glu Asp Cys Ala Phe Gln Glu Glu
            115                 120                 125

Ile Ser Ser Gly Tyr Asn Val Tyr Arg Ser Thr Thr His His Leu Pro
130                 135                 140

Val Ser Leu Ser Ser Ala Lys Gln Arg His Leu Tyr Lys Thr Arg Gly
145                 150                 155                 160

Phe Leu Pro Leu Ser His Phe Leu Pro Val Leu Pro Leu Ala Ser Glu
            165                 170                 175

Glu Thr Ala Ala Leu Gly Asp His Pro Glu Ala Asp Leu Phe Ser Pro
            180                 185                 190

Pro Leu Glu Thr Asp Ser Met Asp Pro Phe Gly Met Ala Thr Lys Leu
            195                 200                 205

Gly Pro Val Lys Ser Pro Ser Phe Gln Lys
        210                 215

<210> SEQ ID NO 9
<211> LENGTH: 218
<212> TYPE: PRT
<213> ORGANISM: Rattus norvegicus

<400> SEQUENCE: 9

Met Ala Arg Lys Trp Ser Gly Arg Ile Val Ala Arg Ala Leu Val Leu
1               5                   10                  15

Ala Thr Leu Trp Leu Ala Val Ser Gly Arg Pro Leu Val Gln Gln Ser
            20                  25                  30

Gln Ser Val Ser Asp Glu Gly Pro Leu Phe Leu Tyr Gly Trp Gly Lys
            35                  40                  45

Ile Thr Arg Leu Gln Tyr Leu Tyr Ser Ala Gly Pro Tyr Val Ser Asn
    50                  55                  60

Cys Phe Leu Arg Ile Arg Ser Asp Gly Ser Val Asp Cys Glu Glu Asp
65                  70                  75                  80

Gln Asn Glu Arg Asn Leu Leu Glu Phe Arg Ala Val Ala Leu Lys Thr
                85                  90                  95

Ile Ala Ile Lys Asp Val Ser Ser Val Arg Tyr Leu Cys Met Ser Ala
                100                 105                 110

Asp Gly Lys Ile Tyr Gly Leu Ile Arg Tyr Ser Glu Asp Cys Thr
            115                 120                 125

Phe Arg Glu Glu Met Asp Cys Leu Gly Tyr Asn Gln Tyr Arg Ser Met
130                 135                 140

Lys His His Leu His Ile Ile Phe Ile Lys Ala Lys Pro Arg Glu Gln

```
        145                 150                 155                 160
Leu Gln Gly Gln Lys Pro Ser Asn Phe Ile Pro Ile Phe His Arg Ser
                    165                 170                 175

Phe Phe Glu Ser Thr Asp Gln Leu Arg Ser Lys Met Phe Ser Leu Pro
                    180                 185                 190

Leu Glu Ser Asp Ser Met Asp Pro Phe Arg Met Val Glu Asp Val Asp
                195                 200                 205

His Leu Val Lys Ser Pro Ser Phe Gln Lys
            210                 215

<210> SEQ ID NO 10
<211> LENGTH: 218
<212> TYPE: PRT
<213> ORGANISM: Mus musculus

<400> SEQUENCE: 10

Met Ala Arg Lys Trp Asn Gly Arg Ala Val Ala Arg Ala Leu Val Leu
1               5                   10                  15

Ala Thr Leu Trp Leu Ala Val Ser Gly Arg Pro Leu Ala Gln Gln Ser
                20                  25                  30

Gln Ser Val Ser Asp Glu Asp Pro Leu Phe Leu Tyr Gly Trp Gly Lys
            35                  40                  45

Ile Thr Arg Leu Gln Tyr Leu Tyr Ser Ala Gly Pro Tyr Val Ser Asn
        50                  55                  60

Cys Phe Leu Arg Ile Arg Ser Asp Gly Ser Val Asp Cys Glu Glu Asp
65                  70                  75                  80

Gln Asn Glu Arg Asn Leu Leu Glu Phe Arg Ala Val Ala Leu Lys Thr
                85                  90                  95

Ile Ala Ile Lys Asp Val Ser Ser Val Arg Tyr Leu Cys Met Ser Ala
            100                 105                 110

Asp Gly Lys Ile Tyr Gly Leu Ile Arg Tyr Ser Glu Glu Asp Cys Thr
        115                 120                 125

Phe Arg Glu Glu Met Asp Cys Leu Gly Tyr Asn Gln Tyr Arg Ser Met
    130                 135                 140

Lys His His Leu His Ile Ile Phe Ile Gln Ala Lys Pro Arg Glu Gln
145                 150                 155                 160

Leu Gln Asp Gln Lys Pro Ser Asn Phe Ile Pro Val Phe His Arg Ser
                    165                 170                 175

Phe Phe Glu Thr Gly Asp Gln Leu Arg Ser Lys Met Phe Ser Leu Pro
                    180                 185                 190

Leu Glu Ser Asp Ser Met Asp Pro Phe Arg Met Val Glu Asp Val Asp
                195                 200                 205

His Leu Val Lys Ser Pro Ser Phe Gln Lys
            210                 215
```